US006958161B2

(12) United States Patent
Hayes et al.

(10) Patent No.: US 6,958,161 B2
(45) Date of Patent: Oct. 25, 2005

(54) MODIFIED RELEASE COATED DRUG PREPARATION

(75) Inventors: David Hayes, Rostrevor (AU); Angelo LoPore, Magill (AU); Stefan Lukas, Manningham (AU); Eugene Quinn, Prospect (AU)

(73) Assignee: F H Faulding & Co Limited, Underdale (AU)

( * ) Notice: Subject to any disclaimer, the term of this patent is extended or adjusted under 35 U.S.C. 154(b) by 247 days.

(21) Appl. No.: 10/120,376

(22) Filed: Apr. 12, 2002

(65) Prior Publication Data

US 2003/0199480 A1 Oct. 23, 2003

(51) Int. Cl.[7] .......................... A61K 9/22; A61K 9/32; A61K 9/36; A61K 9/58; A61K 9/62

(52) U.S. Cl. ...................... 424/475; 424/458; 424/459; 424/461; 424/462; 424/463; 424/474; 424/468; 424/469; 424/480; 424/482; 424/490; 424/494; 424/497

(58) Field of Search ................. 424/458, 459, 424/461, 462, 463, 474, 470, 468, 469, 480, 482, 490, 494, 497, 475

(56) References Cited

U.S. PATENT DOCUMENTS

| | | | |
|---|---|---|---|
| 4,086,332 A | | 4/1978 | Armstrong |
| 4,432,966 A | | 2/1984 | Zeitoun et al. |
| 4,574,080 A | | 3/1986 | Roswall et al. |
| 4,666,897 A | | 5/1987 | Golub et al. |
| 4,713,248 A | | 12/1987 | Kjorn es et al. |
| 4,716,041 A | | 12/1987 | Kjornaes et al. |
| 4,816,259 A | * | 3/1989 | Matthews et al. .......... 424/463 |
| 4,837,030 A | | 6/1989 | Valorose, Jr. et al. |
| 4,853,375 A | | 8/1989 | Krupin et al. |
| 4,882,169 A | | 11/1989 | Ventouras |
| 4,925,833 A | | 5/1990 | McNamara et al. |
| 4,946,686 A | | 8/1990 | McClelland et al. |
| 4,950,484 A | | 8/1990 | Olthoff et al. |
| 4,952,402 A | | 8/1990 | Sparks et al. |
| 5,006,346 A | | 4/1991 | Edgren et al. |
| 5,045,538 A | | 9/1991 | Schneider et al. |
| 5,051,262 A | | 9/1991 | Panoz et al. |
| 5,085,869 A | | 2/1992 | Olthoff et al. |
| 5,133,974 A | | 7/1992 | Paradissis et al. |
| 5,188,836 A | | 2/1993 | Muhammad et al. |
| 5,211,958 A | | 5/1993 | Akkerboom et al. |
| 5,225,202 A | * | 7/1993 | Hodges et al. .............. 424/480 |
| 5,258,372 A | | 11/1993 | Levy |
| 5,260,069 A | | 11/1993 | Chen |
| 5,262,173 A | | 11/1993 | Sheth et al. |
| 5,277,916 A | | 1/1994 | Dwyer et al. |
| 5,283,065 A | | 2/1994 | Doyon et al. |
| 5,348,748 A | | 9/1994 | Sheth et al. |
| 5,366,733 A | | 11/1994 | Brizzolara et al. |
| 5,409,711 A | | 4/1995 | Mapelli et al. |
| 5,413,777 A | | 5/1995 | Sheth et al. |
| 5,445,829 A | | 8/1995 | Paradissis et al. |
| 5,472,708 A | | 12/1995 | Chen |
| 5,536,507 A | | 7/1996 | Abramowitz et al. |
| 5,576,021 A | | 11/1996 | Andoh et al. |
| 5,663,201 A | * | 9/1997 | Lowther et al. ............ 514/507 |

(Continued)

FOREIGN PATENT DOCUMENTS

EP 0 630 646 A1 * 12/1994 ............ A61K/9/50

*Primary Examiner*—James M. Spear
(74) *Attorney, Agent, or Firm*—Birch, Stewart, Kolasch & Birch, LLP

(57) ABSTRACT

A modified release preparation having one or more coated core elements, each core element including an active ingredient and having a modified release coating, wherein a stabilising coat is provided between each core element and its modified release coating so that, upon in vitro dissolution testing, the amount of active ingredient released at any time on a post-storage dissolution profile is within 40 percentage points of the amount of active ingredient released at any time on a pre-storage dissolution profile.

24 Claims, 2 Drawing Sheets

Rate of drug release of pellets immediately after production and after various lengths of storage.

U.S. PATENT DOCUMENTS

| | | |
|---|---|---|
| 5,668,122 A | 9/1997 | Fife et al. |
| 5,725,883 A | 3/1998 | Staniforth et al. |
| 5,741,524 A | 4/1998 | Staniforth et al. |
| 5,780,055 A | 7/1998 | Habib et al. |
| 5,789,395 A | 8/1998 | Amin et al. |
| 5,800,836 A | 9/1998 | Morella et al. |
| 5,858,409 A | 1/1999 | Karetny et al. |
| 5,858,412 A | 1/1999 | Staniforth et al. |
| 5,866,166 A | 2/1999 | Staniforth et al. |
| 5,908,838 A | 6/1999 | Gans |
| 5,948,438 A | 9/1999 | Staniforth et al. |
| 6,015,804 A | 1/2000 | Golub et al. |
| 6,077,533 A | 6/2000 | Oshlack et al. |
| 6,106,865 A | 8/2000 | Staniforth et al. |
| 6,120,802 A | 9/2000 | Breitenbach et al. |
| 6,277,393 B1 | 8/2001 | Yrjanheikki et al. |
| 2001/0004458 A1 | 6/2001 | Opitz et al. |
| 2001/0046964 A1 | 11/2001 | Percel et al. |
| 2002/0022608 A1 | 2/2002 | Duncan et al. |

\* cited by examiner

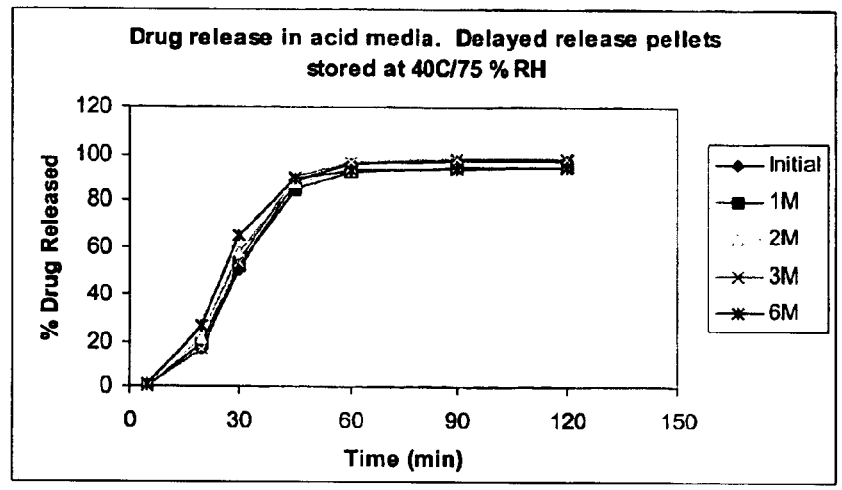
Figure 1: Rate of drug release of pellets immediately after production and after various lengths of storage.
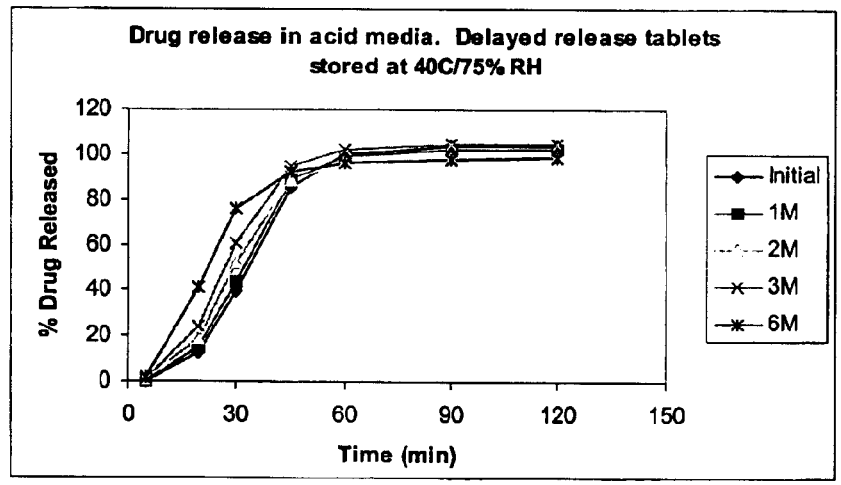
Figure 2: Rate of drug release of *tablets* containing the pellets of Example 1 immediately after production and after various lengths of storage.

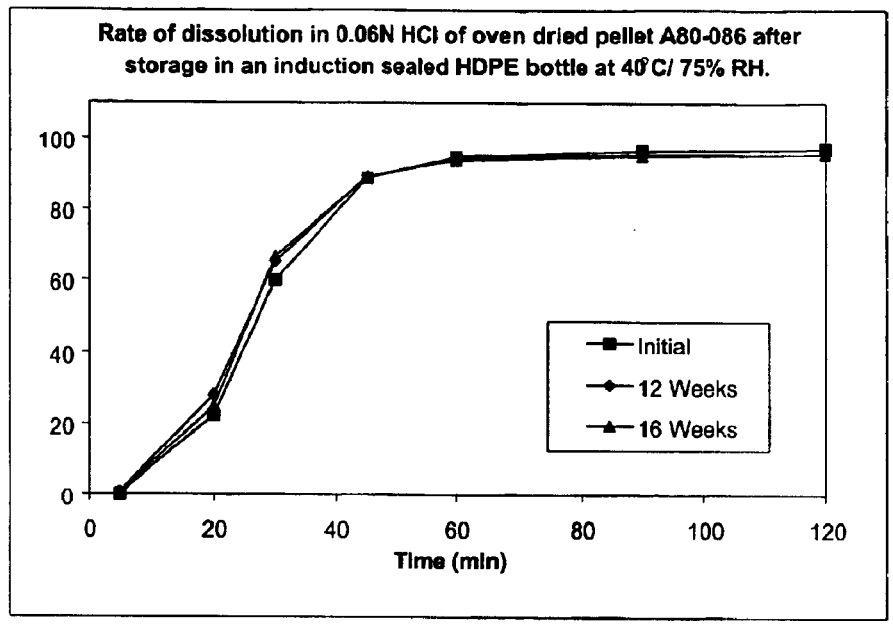
Figure 3: Rate of drug release of (cured) pellets from Example 1, immediately after production and after various lengths of storage.
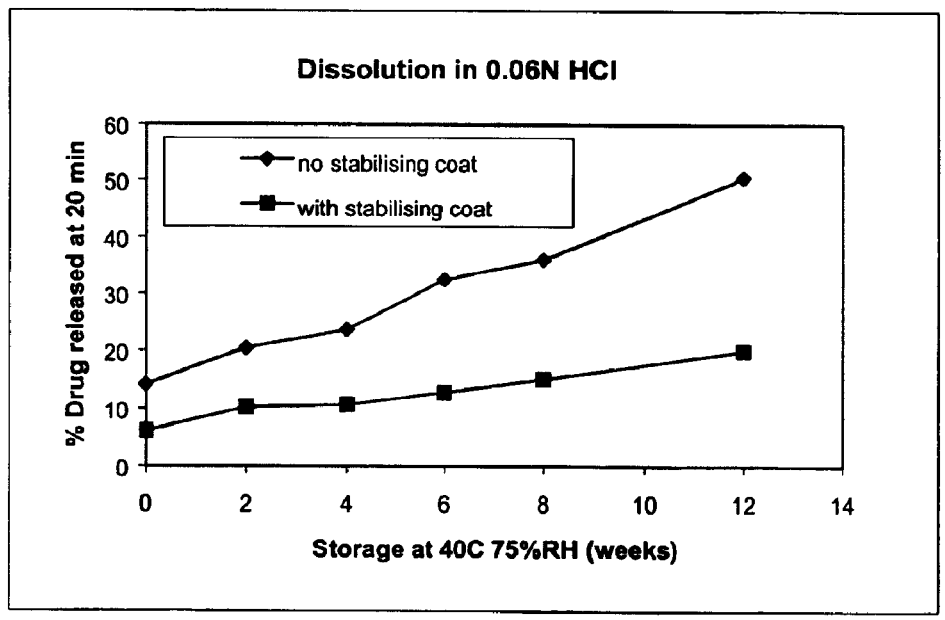
Figure 4: Comparative drug released at 20 minutes of tablets containing pellets with and without a stabilising coat from Comparative Example 1.

MODIFIED RELEASE COATED DRUG PREPARATION

FIELD OF THE INVENTION

The present invention relates to improvements in modified release preparations, such as modified release pharmaceutical preparations.

BACKGROUND OF THE INVENTION

Modified release preparations are those that provide an in vivo release profile (a 'modified release') of an active ingredient, such as a pharmaceutically active ingredient, that is different from the in vivo release profile of the active ingredient without the modification (an 'immediate release'). The modified release may be such as a delayed, extended, pulsed or sustained release. The modification of the release may be desired for a number of reasons, such as for minimising the side effects of the drug or for decreasing the frequency of dosing to improve patient compliance.

As with all pharmaceutical preparations, an important aspect of the manufacture of modified release preparations is their stability over extended periods of time, which is often referred to as 'shelf life'. Typically, a preparation's shelf life is linked to two aspects; firstly, the stability of the ingredients themselves, namely the maintenance of their chemical, microbiological, therapeutic and toxicological properties over time; and secondly, the maintenance over time of the originally intended rate of drug release from the dosage form. The present invention is directed towards this second aspect of stability.

All pharmaceuticals must have an appropriate shelf life, being the time for which it can be guaranteed that the preparation has the same properties that it had at the time it was manufactured. These properties may be such as impurity content, drug degradants or rate of drug release. For oral preparations, this shelf life is usually at least 18 months.

However, it has been found for some modified release preparations that, after storage, the release profile alters by a significant amount. For example, some delayed release preparations that have been formulated with an enteric coating so as to release only small amounts of active (10% or less) after 20 minutes might release up to 80% of active by 20 minutes after the preparation has been stored. This increase in rate of release can detract from the utility and effectiveness of the product.

It is an aim of the present invention to provide a modified release preparation that is stable, in that the release profile after storage of a preparation in accordance with the invention will be substantially the same as the release profile of the preparation before storage.

SUMMARY OF THE INVENTION

The present invention provides a modified release preparation having one or more coated core elements, each core element including an active ingredient and having a modified release coating, wherein a stabilising coat is provided between each core element and its modified release coating so that, upon in vitro dissolution testing, the amount of active ingredient released at any time on a post-storage dissolution profile is within 40 percentage points of the amount of active ingredient released at any time on a pre-storage dissolution profile.

In a preferred form, the amount of active ingredient released at the majority of time points on the post-storage dissolution profile is within 30 percentage points of the amount of active ingredient released at the same time on the pre-storage dissolution profile, although more preferably it will be within 20 percentage points and more preferably within 10 percentage points. In this respect, reference to 'percentage points' is reference to a cumulative amount of active ingredient released. Thus, if immediately after production (represented by the pre-storage dissolution testing referred to above) a formulation releases 10% of the total active ingredient, at the same time in the post-storage dissolution testing, the formulation will release no more than 40% of the total amount of active, more preferably no more than 30% and most preferably no more than 20%.

With regard to the above reference to 'the majority of time points on the post storage dissolution profile', it will be appreciated by a skilled addressee that there may be irregular spikes at some time points on the profile for some tablets for a wide range of reasons. Indeed, it is possible that at some time points the amount of release may be outside the more preferred 30, 20 and 10 percentage point ranges. Preferably, such irregularities will occur only as isolated incidents for individual tablets, and preferably at time points that are not in the more critical early dissolution times, such as in the first 20 minutes after commencement. Indeed, it is to be understood that a post storage dissolution profile that substantially complies with these requirements will be considered to be indicative of a preparation within the scope of the present invention.

With further reference to determining whether a preparation is in accordance with the present invention, the in vitro dissolution testing should be carried out on preparations subjected to a standardised storage test based on the accelerated conditions of storage referred to in the United States' Food & Drug Administration (FDA) guidelines. The guidelines define accelerated conditions as the storage of a pharmaceutical product (namely, in its container and package) at 75% relative humidity (RH) and 40° C. for 6 months. However, it has also recently been proposed that suitable accelerated conditions for such pharmaceutical products would be storage at 60% RH and 30° C. for 12 months.

These sets of conditions are deemed equivalent for the purpose of the in vitro dissolution testing required to be conducted to determine whether a preparation falls within the scope of the present invention. Indeed, a product that meets the above criteria after either of these storage conditions is considered to be within the scope of the present invention.

Further, the in vitro dissolution testing should also of course be conducted so as to provide a dissolution profile, being a plot of percentage of active ingredient released in a prescribed aqueous media as a function of time. Such a dissolution profile may be measured utilising the standard USP XXIV 2000—Apparatus 1 (baskets).

Modified release preparations in accordance with the present invention will typically be such as to provide a delayed release of the active ingredient, with reference to the active ingredient's dissolution profile. In this respect, where the modified release is such as to provide a delayed release (generally referred to as a 'delayed release preparation') the preparation aims to slow the release of the active in the stomach to minimise the side effects of the active that may be caused by release of the active in the stomach. Such side effects include nausea and gastrointestinal irritation.

Most delayed release preparations aim for the drug to be released in the upper regions of the small intestines, for a number of reasons, as follows:

the drug is able to start working as soon as possible after ingestion without side effects caused by drug being released in the stomach;

the conditions in the upper small intestine are usually optimum for drug absorption; and to avoid acid degradation of the drug in the stomach.

By way of explanation, the stomach contents of healthy individuals who have eaten average meals usually have a residence time of 30 minutes to an hour and are at a pH in the stomach usually in the range of 1 to 3. The stomach contents then move to the intestines where the pH usually ranges from 4 to 7, where a rapid release of the active ingredient is desired to allow rapid and complete absorption of the active ingredient. There may be release of the drug in the stomach after a lag period, if the residence time is longer or the stomach conditions are different from usual, but the release will be at a much slower rate than an immediate release preparation, so the high localised concentrations that cause nausea and irritation do not occur.

Therefore, an ideal delayed release profile has minimal active ingredient released in the low pH of the stomach for approximately 20 minutes, and then when put in an aqueous solution with a pH of at least 4, 100% of the active ingredient is released within 60 minutes. Realistically, it is difficult to get a preparation that releases no active ingredient in the stomach and then all of the active ingredient in the intestines, so a realistic profile would be for less than 10% of the active ingredient to be released in a pH of about 1.2 after 20 minutes and at least 90% of the active ingredient released after 60 minutes in a pH of at least 5 in in vitro tests. In one preferred form of the invention no more than 20% of the active ingredient is released in a pH of about 1.2 by 20 minutes and at least 80% of the active ingredient in a pH of at least 5 by 60 minutes. For the purposes of in vitro testing, a release profile may be determined at pH 1.2 using a 0.6N hydrochloric acid solution, and at pH 5.5 using a phosphate buffer.

Such a release profile is preferred for some pharmaceutical active ingredients such as antibiotics, or for any drug that can cause nausea or gastrointestinal irritation but that has a narrow absorption window high in the intestinal tract. For example, bisphosphonates are known to cause gastrointestinal ulceration at higher doses, opioid analgesics are known to cause nausea, and very basic drugs can be neutralised by the acidic conditions of the stomach, precipitate and not be absorbed. Additionally, other reactions may take place causing the activity of the drug to be lost.

As mentioned above, an important aspect of the manufacture (and also the regulatory review and approval) of all modified release preparations, including delayed release preparations, concerns their stability over extended periods of time, particularly their ability to provide a dissolution profile that is largely unaffected during the intended shelf life of the preparation.

In this respect, it has been found that the dissolution profile for a modified release preparation in accordance with the present invention is significantly less affected after being subjected to storage. This gives rise to a high degree of confidence, when determining an expiration date for a pharmaceutical product made from the preparation, that the desired release profile will still be maintained through to the expiration date. It also permits an extended expiration date to be set.

By way of example, for a particular delayed release preparation (in this instance being a preparation with doxycycline as the active ingredient), the amount of active ingredient released at various times might be as follows (in vitro dissolution testing conducted pre-storage in a pH 1.2 solution):

| Time (min) | % Released |
| --- | --- |
| 0 | 0 |
| 10 | 8 |
| 20 | 20 |
| 30 | 60 |
| 40 | 75 |
| 60 | 90 |
| 90 | 95 |

For this example, a preparation in accordance with the present invention would desirably release amounts of active in the following ranges (namely, within 40 percentage points) after exposure to accelerated conditions of storage (in vitro dissolution testing conducted post-storage in a pH 1.2 solution):

| Time (min) | % Released |
| --- | --- |
| 0 | 0 |
| 10 | 0 to 48 |
| 20 | 0 to 60 |
| 30 | 20 to 100 |
| 40 | 35 to 100 |
| 60 | 50 to 100 |
| 90 | 55 to 100 |

Most preferably in this example, the amounts of active released after exposure to accelerated conditions of storage (again, in vitro dissolution testing conducted post-storage in a pH 1.2 solution) would desirably be in the following ranges (namely within 20 (but preferably 10) percentage points for times up to and including about 20 minutes, and within 30 (but again preferably 10) percentage points thereafter):

| Time (min) | % Released |
| --- | --- |
| 0 | 0 |
| 10 | 0 to 28 |
| 20 | 0 to 40 |
| 30 | 30 to 90 |
| 40 | 45 to 100 |
| 60 | 60 to 100 |
| 90 | 65 to 100 |

A modified release preparation in accordance with the present invention should thus satisfy the various national regulatory and approval requirements in relation to shelf life and stability.

DETAILED DESCRIPTION OF THE INVENTION

The preferred dosage forms for the modified release preparations of the present invention will be formulated from a plurality of pellets. Each pellet will preferably be one of the coated core elements mentioned above, being a core element containing an active ingredient and having a modified release coating, there being a stabilising coat between the core element and the modified release coating.

In one form, a plurality of such coated core elements may be provided in a capsule. In a more preferred form, a plurality of such coated core elements (or a plurality of suitably agglomerated coated core elements) may be compressed, along with suitable normal tablet excipients, and provided as a tablet. It is also possible for the dosage form to be a single coated core element, large enough itself to be referred to as a tablet.

While suitable tabletting excipients will be known to a person skilled in the art, the optimal formulation of the tablet involves balancing the need for content uniformity (namely, making sure the same number of pellets is present in each tablet and therefore the same amount of active ingredient is present in each tablet) and the amount of excipients required to protect the friable coating of the modified release pellets.

In this respect, if the number of pellets is too low, there will be problems with content uniformity, while if the number of pellets is too high there will not be enough tabletting excipients to cushion the pellets during compression into a tablet and the modified release coating will be compromised. Therefore, the percentage of pellets in each tablet is ideally in the range of 20 to 40% (more preferably 25 to 35%, but most preferably about 30%) by weight of the total dosage weight.

When forming tablets, a person skilled in the art would recognise that when a tablet is being formulated it is necessary to include excipients to fulfil the function of a filler, a binder, a disintegrant and a lubricant along with the active ingredient. In the present invention the active ingredient is present in the form of pellets with a modified release coating. Optionally, the tablet may also contain other ingredients such as flavours, colours etc.

The range of materials that are suitable for use as fillers, disintegrants, binders and lubricants will be well known to the person skilled in the art.

In a final tablet formulation, the core pellets may be present in an amount of 5 to 50% w/w, based on the total tablet weight. Below a level of about 5% w/w core pellets in the tablet formulation there may be potency problems or the tablet may be too large to swallow. Above a level of about 50% w/w core pellets in the tablet formulation the tablet may contain too many pellets and insufficient binder and the pellet coating may be compromised or the pellets may stick together under the compression forces required to form the tablets.

Preferably lactose and/or starch are used as fillers in the tablet. The total amount of lactose plus starch present in the tablet can range between 50 to 95% w/w, based on the total weight of the tablet. A suitable disintegrant for use in a tablet of the present invention is crospovidone, and this may be present in a range of 0 to 15% w/w, based on the total weight of the tablet. A suitable lubricant for use in a tablet of the invention is magnesium stearate and the lubricant may be present in a range of between 0.2 to 1.0% w/w, based on the total weight of the tablet.

The core elements provide the active ingredient. The active ingredient may be embodied within and through the core element, and may be combined with or without the normal excipients, additives and fillers. Alternatively, the active ingredient may itself be coated onto, for example, an inert bead to provide the core element. Preferably, before coating with the stabilising coat and the modified release coating, the core elements each have a diameter in the range of 50 microns to 2000 microns. If a single core is to be used the size of the core will preferably range from 5 mm to 20 mm.

The core elements may be formed by any suitable method. For example, the core elements may be formed by spheronisation onto seed core, extrusion, marumerisation, or rotogranulation. Preferably, the core elements will be formed by extrusion.

It will be appreciated that the core elements may contain any suitable or required additives, such as excipients, fillers or other ingredients. Preferably, the composition of the core element is carefully determined to further enhance the likelihood of the post-storage dissolution profile being acceptably similar to the dissolution profile pre-storage.

In one preferred form of the invention the core is formed by extrusion using an extruding solution.

The core material to be extruded preferably contains the active ingredient, a binder, a wicking agent and a lubricant.

Preferably the binder is microcrystalline cellulose, however powdered cellulose or any of the co-processed microcrystalline celluloses that contain additives such as silica, may be used. Preferably the amount of binder used ranges between 8 to 45% by weight, based on the total weight of the core.

It is preferable to have a wicking agent or water transport modifier in the core formulation. A wicking agent allows water to be transported throughout the core and aids in the release of all of the active ingredient in the core. Preferably, the wicking agent is selected from lactose, starch or sorbitol. Most preferably the wicking agent is lactose. Preferably the wicking agent is present in an amount of from 0 to 45% by weight, based on the total weight of the core.

Optionally, the core formulation may also include a lubricant, and a number of suitable lubricants will be known to the person skilled in the art. In a preferred form of the present invention the lubricant is selected from sodium lauryl sulphate or magnesium stearate. Preferably the lubricant is present in an amount ranging from 0 to 10% by weight, based on the total weight of the core.

The active ingredient may be present in the core element in any suitable amount, and for instance may be provided in an amount from 5 to 95% by weight, preferably from 20 to 80% by weight, based on the total weight of the core element.

A person skilled in the art of making cores for pellets will be familiar with other materials that may be used to provide the same physical effects as the binder, the wicking agent or the lubricant.

The active ingredient may be any suitable and desirable pharmaceutical, medicament or chemical. For example, the active ingredient may be acid salts of doxycycline, tetracycline, oxytetracycline, minocycline, chlortetracycline, or demeclocycline. Any active ingredient that causes nausea or irritation, but also has a narrow absorption window high in the intestines will benefit from the application of this invention.

The stabilising coat is a physical barrier between the active ingredient and the modified release coating. The stabilising coat may also be referred to as a seal coat or an intermediary layer.

The purpose of the stabilising coat is to keep the active ingredient and the modified release coating separated. In this respect, it is believed that the stabilising coat slows migration of moisture or solvent between the modified release coating and the active ingredient. Whilst the stabilising coat will preferably keep the active ingredient separated from the modified release coating during storage, the stabilising coat will ideally not interfere significantly with the rate of release of the active ingredient, and therefore should be at least semi-permeable in aqueous media and may even be soluble. Indeed, the stabilising coat is intended to keep migration of core materials to a minimum such that their interaction with coating materials is reduced or prevented, whilst still allowing for release of core materials in an aqueous environment.

The stabilising coat may thus be any suitable material which makes an inert barrier between the core element, or the active ingredient containing layer, and the modified release coating, and may be water soluble, water swellable or water permeable polymeric or monomeric materials. Examples of such materials include, but are not limited to, hydroxypropylmethyl cellulose, hydroxypropyl cellulose, polyvinyl pyrrolidone, polyethylene glycol or methacrylate based polymers (e.g. Eudragit® RS or Eudragit® RL).

Preferably the stabilising coat includes a water-soluble polymer that does not interfere with the release of the active ingredient, and talc or another agent that performs the same function as talc. The water soluble polymer and talc may be present in the range of between 9 parts polymer to 1 part talc, through to 1 part polymer to 9 parts talc.

The modified release coating may also be any suitable coating material, or combination of coating materials, that will provide the desired modified release profile. For example, coatings such as enteric coatings, semi-enteric coatings, delayed release coatings or pulsed release coatings may be desired. In particular, a coating will be suitable if it provides an appropriate lag in active release prior to the rapid release at a rate essentially equivalent to immediate release of the active ingredient.

In particular, materials such as hydroxypropylmethyl cellulose phthalate of varying grades (and also as an aqueous dispersion), methacrylate based polymers (e.g. Eudragit® L100-55 and Eudragit® L30D) and hydroxypropylmethyl cellulose acetate succinate are all suitable. It is also possible to use a mixture of enteric polymers to produce the modified release coating. It is also possible to use a mixture of enteric polymer with a water permeable, water swellable or water-soluble material.

Suitable water-soluble or water permeable materials include but are not limited to hydroxypropylmethyl cellulose, hydroxypropyl cellulose, polyvinyl pyrrolidone, polyethylene glycol or mixtures thereof.

The modified release coating may contain between 40 to 90% w/w enteric polymer, and between 10 to 60% w/w water-soluble or water permeable material, based on the total weight of the modified release coating. The modified release coating may also contain 0 to 30% w/w of a plasticiser, based on the total weight of the modified release coating.

The polymer coat weight of the modified release coating (as a percentage of the total pellet) will vary depending on the delay desired and the polymer used, but generally will be between and 5%w/w and 20%w/w. By polymer coat weight is meant the polymer and plasticiser in the coating layer, and does not include additives such as talc, which do not significantly affect the release rate of the pellet.

The stabilising coat and the modified release coating may be applied to a core element in any suitable manner, such as by fluidised bed coating, including wurster coating, and rotacoating. In a preferred form, both coats will be applied by wurster coating.

Drying the pellet using any one of a number of drying techniques known in the art, such as oven drying or drying in a fluidised bed apparatus, may further improve stability.

BRIEF DESCRIPTION OF THE DRAWINGS

Various drawings are provided with this specification as a part of the following description of the preferred embodiments. In those drawings:

FIG. 1 illustrates the rate of drug release of the pellets from Example 1, immediately after production and after various lengths of storage;

FIG. 2 illustrates the rate of drug release of tablets containing the pellets from Example 1, immediately after production and after various lengths of storage;

FIG. 3 illustrates the rate of drug release of cured pellets from Example 1, immediately after production and after various lengths of storage;

FIG. 4 illustrates the comparative drug release at 20 minutes of tablets containing pellets with and without a stabilising coat from Comparative Example 1, immediately after production and after various lengths of storage; and

DETAILED DESCRIPTION OF PREFERRED EMBODIMENTS

The present invention will now be described with reference to several examples that illustrate preferred embodiments. However, the following description of the examples is not to limit the generality of the above description.

IN THE EXAMPLES

Examples 1 and 2 exemplify a first preferred embodiment of a preparation in accordance with the invention, with Example 1 directed to pellets and Example 2 directed to tablets formed from those pellets, there being supporting data illustrating the improved stability for those preparations;

Example 3 exemplifies the pellets of Example 1 after having been subjected to a drying step, and also provides supporting data illustrating improved stability;

Example 4 exemplifies a second preferred embodiment of a preparation in accordance with the invention, being directed to tablets formed from pellets, which preparation is also expected to provide improved stability; and Comparative Example 1 exemplifies a third preferred embodiment of a preparation in accordance with the invention, and provides comparative data for the stability of tablets containing a stabilising coat relative to those that do not contain a stabilising coat.

Example 1

Core Element Preparation

| Ingredient | Weight % |
| --- | --- |
| Doxycycline Hyclate | 80 |
| Microcrystalline Cellulose | 10 |
| Lactose | 10 |

The core element is formed in a wet granulation process using a saturated solution of sodium chloride and in a high shear mixer.

The mixture is then extruded using a screen size of between 0.4 and 1.5 mm. The extrudate is then marumerised to produce rounded core elements. The core elements are dried in a fluidised bed or an oven.

Stabilising Coat Application

A stabilising coat is applied to the core elements using a fluidised bed coating process. The stabilising coat consists of hydroxypropylmethyl cellulose and talc in a 2:1 mixture. The aim polymer coat weight (the weight of the polymer only, not including the talc) is between 3 and 5% of the total weight of the core element and the stabilising coat. The polymer coat weight will vary due to a number of factors, such as the efficiency of the coating process, the batch of raw materials etc.

Modified Release Coating Application

| Ingredient | Weight % |
| --- | --- |
| Hydroxypropylmethyl cellulose phthalate | 67 |
| Hydroxypropylmethyl cellulose | 16 |
| Triethyl citrate | 17 |

The modified release coating is applied to the stabilising coated core elements using a fluidised bed coating process to form pellets. The aim polymer coat weight is 15% of the total weight of the pellet.

The in vitro release of the pellets was tested using USP XXIV 2000—Apparatus 1 (baskets) and the resulting dissolution profile (pre-storage being referred to as 'initial') is shown in FIG. 1, together with various post-storage dissolution profiles (from 1 month to 6 months).

The following table shows the raw data for FIG. 1 from which it can be seen that, after storage for 6 months at accelerated conditions, the change in the amount of drug released at most time points is less than 10 percentage points, and at all time points is less than 20 percentage points. It can also be seen that during the more critical early time period of up to 20 minutes, the change in the amount of drug released is within the lower range.

| Time Point (mins) | Initial | 1 month | 2 months | 3 months | 6 months | Change (percentage points) |
| --- | --- | --- | --- | --- | --- | --- |
| 5 | 0 | 0.3 | 0.2 | 0.1 | 0.4 | <10 |
| 20 | 16.9 | 18.9 | 21.2 | 16.9 | 26.4 | <10 |
| 30 | 50.9 | 51.7 | 57.2 | 53.3 | 64.9 | <20 |
| 45 | 88.6 | 84.9 | 87.4 | 89.5 | 89.3 | <10 |
| 60 | 95.8 | 92.4 | 92.6 | 96.5 | 93.1 | <10 |
| 90 | 97.7 | 94 | 93.7 | 97.9 | 93.9 | <10 |
| 120 | 97.7 | 94.2 | 93.9 | 98.2 | 94.1 | <10 |

Example 2

The pellets prepared in Example 1 were formulated into tablets.

| Ingredient | Weight % |
| --- | --- |
| Pellets | 31.5 (equivalent to the desired dose of active) |
| Lactose | 55 |
| Starch | 10 |
| Crospovidone | 3 |
| Magnesium Stearate | 0.6 |

The ingredients were combined in a tumble blender and then tabletted using a rotary tablet press.

The in vitro release of the tablets was tested using USP XXIV 2000—Apparatus 1 (baskets) and the resulting dissolution profile (pre-storage being referred to as 'initial') is shown in FIG. 2, together with various post-storage dissolution profiles (from 1 month to 6 months).

The following table shows the raw data for the graph in FIG. 2 from which it can be seen that, after storage for 6 months at accelerated conditions, the change in the amount of drug released at most time points is less than 30 percentage points (and indeed for most is less than 10 percentage points), and at all time points is less than 40 percentage points. It can also be seen that during the more critical early time period of up to 20 minutes, the change in the amount of drug released is within the lower range of 30 percentage points.

| Time Point (min) | Initial | 1 month | 2 months | 3 months | 6 months | Change (percentage points) |
| --- | --- | --- | --- | --- | --- | --- |
| 5 | 0 | 0.3 | 0.5 | 0.6 | 1.6 | <10 |
| 20 | 12.3 | 15 | 18.6 | 24.1 | 40.8 | <30 |
| 30 | 39.2 | 43.1 | 52.2 | 60.4 | 75.7 | <40 |
| 45 | 85.1 | 88.1 | 88.4 | 94.6 | 92.5 | <10 |
| 60 | 100.2 | 99.4 | 96.4 | 102 | 96.1 | <10 |
| 90 | 103.6 | 102.2 | 98.6 | 104.3 | 97.8 | <10 |
| 120 | 104 | 102.4 | 98.9 | 104.7 | 98.3 | <10 |

Example 3

The pellets of Example 1 were additionally cured in an oven at 50° C. for 5 days before storage, and in vitro dissolution provided the pre-storage and post-storage dissolution profiles shown in FIG. 3.

Example 4

Core Element Preparation

The core elements are formed using a wet granulation technique with the solution being a saturated solution of sodium chloride. The core elements are extruded to be between 0.4 and 1.5 mm wide. They then are marumerised and dried to provide a pellet of formulation:

| Ingredient | Weight % |
| --- | --- |
| Doxycycline hyclate | 71 |
| Sodium chloride | 10 |
| Microcrystalline cellulose | 9 |
| Lactose monohydrate | 9 |
| Sodium lauryl sulphate | 0.6 |

Once the pellets are dried they are coated, using a fluidised bed, with the stabilising coat as below. Once the stabilising coat is dry, the coated core element (the pellet) is then coated with the modified release coat, as below, again using a fluidised bed process. The complete pellets are then tabletted with tabletting excipients as described below.

Stabilising Coat

| Ingredient | Weight % |
| --- | --- |
| Hydroxypropylmethylcellulose | 66 |
| Talc | 34 |

Modified Release Coat

| Ingredient | Weight % |
|---|---|
| Hydroxypropylmethyl cellulose phthalate | 67 |
| Hydroxypropylmethyl cellulose | 16 |
| Triethyl citrate | 17 |

Tablet Preparation

| Ingredient | Weight % |
|---|---|
| Pellets | 30.0 (equivalent to desired dose of active) |
| Lactose | 56.6 |
| Starch | 10 |
| Crospovidone | 3 |
| Magnesium Stearate | 0.4 |

These ingredients are compressed into an oval shaped tablet. There is no break-line or film coating. The final tablet weight is approximately 700 mg.

Comparative Example 1

In vitro dissolution studies of tablets containing pellets with and without a stabilising coat provided the comparative dissolution profiles shown in FIG. 4.

Pellets were formed according to the method described in Example 4 with the exception of the extruding solution being water. The pellets had the following formulation.

| Ingredient | With Stabilising Coat Weight % | Without Stabilising Coat Weight % |
|---|---|---|
| Core | | |
| Doxycycline hyclate | 70.9 | 66.4 |
| Lactose | 8.9 | 8.3 |
| Microcrystalline cellulose | 8.9 | 8.3 |
| Stabilising Coat | | |
| Hydroxypropylmethyl cellulose | — | 3.5 |
| Talc | — | 1.7 |
| Modified Release Coat | | |
| Hydroxypropylmethyl cellulose phthalate | 7.7 | 8.0 |
| Hydroxypropylmethyl cellulose | 1.9 | 2.0 |
| Diethyl phthalate | 1.8 | 1.9 |

The pellets were then tabletted as in Example 2 to provide tablets with the following formulation.

| Ingredient | With Stabilising Coat Weight % | Without Stabilising Coat Weight % |
|---|---|---|
| Pellets | 28.9 | 26.8 |
| MCC | 52.6 | 55.7 |
| Lactose | 14.6 | 13.9 |
| Crospovidone | 3.6 | 2.9 |
| Magnesium Stearate | 0.3 | 0.6 |

The tablets were stored in a controlled environment at a temperature of 40° C. and 75% relative humidity for 12 weeks and the in vitro dissolution properties of the two tablet formulations were measured.

The following table shows the comparative raw data for the graph in FIG. 4 showing the percent released at 20 minutes of tablets containing pellets with and without a stabilising coat.

| | % Release at 20 min. | |
|---|---|---|
| Time (weeks) | No stabilizing coat | With stabilizing coat |
| 0 | 14.16 | 6.1 |
| 2 | 20.5 | 10.3 |
| 4 | 23.74 | 10.71 |
| 6 | 32.5 | 12.8 |
| 8 | 36.15 | 15.13 |
| 12 | 50.5 | 20 |

Finally, there may be other variations and modifications made to the preparations and methods described herein that are also within the scope of the present invention.

What is claimed is:

1. A modified release preparation having one or more coated core elements, each core element comprising an active ingredient selected from the group consisting of the acid salts of doxycycline, tetracycline, oxytetracycline, minocycline, chlortetracycline or demeclocycline and having a modified release coating, wherein a stabilising coat is provided between each core element and its modified release coating so that, upon in vitro dissolution testing, the amount of active ingredient released at any time on a post-storage dissolution profile is within 40 percentage points of the amount of active ingredient released at any time on a pre-storage dissolution profile.

2. The preparation according to claim 1, wherein the amount of active ingredient released at the majority of time points on the post-storage dissolution profile is within 30 percentage points of the amount of active ingredient released at the same time on the pre-storage dissolution profile.

3. The preparation according to claim 1, wherein the amount of active ingredient released at the majority of time points on the post-storage dissolution profile is within 20 percentage points of the amount of active ingredient released at the same time on the pre-storage dissolution profile.

4. The preparation according to claim 1, wherein the amount of active ingredient released at the majority of time points on the post-storage dissolution profile is within 10 percentage points of the amount of active ingredient released at the same time on the pre-storage dissolution profile.

5. The preparation according to claim 1, wherein the modified release coating is a delayed release coating.

6. The preparation according to claim 1, wherein the modified release coating is a delayed release coating suitable to release, in a pre-storage in vitro dissolution, 20% or less of the active ingredient in a pH of about 1.2 by 20 minutes and at least 80% of the active ingredient in a pH of at least 5 by 60 minutes.

7. The preparation according to claim 1, wherein the modified release coating is a delayed release coating suitable to release, in a pre-storage in vitro dissolution, 10% or less of the active ingredient in a pH of about 1.2 by 20 minutes and at least 90% of the active ingredient in a pH of at least 5 by 60 minutes.

8. The preparation according to claim 1, wherein the modified release coating is an enteric coating, a semi-enteric coating, a delayed release coating, a pulsed release coating, a mixture of enteric polymers, or a mixture of an enteric polymer with a water permeable, water swellable or water soluble material.

9. The preparation according to claim 8, wherein the water soluble or water permeable materials are one or a mixture of hydroxypropylmethyl cellulose, hydroxypropyl cellulose, polyvinyl pyrrolidone and polyethylene glycol.

10. The preparation according to claim 1, wherein the modified release coating comprises one or more of hydroxypropylmethyl cellulose phthalate, a pH dependent anionic methacrylate based polymer, or hydroxypropylmethyl cellulose acetate succinate.

11. The preparation according to claim 1, wherein the stabilising coat is at least semi-permeable in aqueous media.

12. The preparation according to claim 1, wherein the stabilising coat is one or a mixture of a water-soluble, water swellable or water permeable polymeric or monomeric material.

13. The preparation according to claim 1, wherein the stabilising coat is one or a mixture of hydroxypropylmethyl cellulose, hydroxypropyl cellulose, polyvinyl pyrrolidone, polyethylene glycol, a pH dependent anionic methacrylate based polymer.

14. A method of administering an active ingredient that, upon administration in an immediate release form, normally causes nausea and gastric irritation, the method comprising administering a modified release preparation in accordance with claim 1.

15. The preparation according to claim 1, the preparation being provided as a plurality of coated core elements in a capsule.

16. The preparation according to claim 1, the preparation being provided as a plurality of coated core elements compressed to form a tablet.

17. The preparation according to claim 16, wherein the percentage of coated core elements in each tablet is in the range of 20 to 40 by weight of the total dosage weight.

18. The preparation according to claim 16, wherein the percentage of coated core elements in each tablet is in the range of 25 to 35% by weight of the total dosage weight.

19. The preparation according to claim 16, wherein the percentage of coated core elements in each tablet is about 30% by weight of the total dosage weight.

20. The preparation according to claim 1, wherein the modified release coating is a delayed release coating, the active ingredient is an acid salt of doxycycline, and the preparation is provided as a plurality of coated core elements compressed to form a tablet.

21. A tablet for oral administration, the tablet being a modified release preparation having one or more coated core elements, each core element comprising an active ingredient comprising an acid salt of doxycycline and having a modified release coating, wherein a stabilising coat is provided between each core element and its modified release coating so that, upon in vitro dissolution testing, the amount of active ingredient released at any time on a post-storage dissolution profile is within 40 percentage points of the amount of active ingredient released at any time on a pre-storage dissolution profile.

22. The tablet according to claim 21, wherein the modified release coating is a delayed release coating.

23. A pellet for use in a dosage form for oral administration, the pellet being a modified release preparation having one or more coated core elements, each core element comprising an active ingredient comprising an acid salt of doxycycline and having a modified release coating, wherein a stabilising coat is provided between each core element and its modified release coating so that, upon in vitro dissolution testing, the amount of active ingredient released at any time on a post-storage dissolution profile is within 40 percentage points of the amount of active ingredient released at any time on a pre-storage dissolution profile.

24. The method according to claim 14, wherein the modified release coating is a delayed release coating, and the active ingredient is an acid salt of doxycycline.

* * * * *

UNITED STATES PATENT AND TRADEMARK OFFICE
CERTIFICATE OF CORRECTION

PATENT NO. : 6,958,161 B2
DATED : October 25, 2005
INVENTOR(S) : David Hayes et al.

It is certified that error appears in the above-identified patent and that said Letters Patent is hereby corrected as shown below:

Title page,
Item [75], Inventors, delete "Angelo LoPore" and replace with -- Angelo Lepore --.

Signed and Sealed this

Fourteenth Day of February, 2006

JON W. DUDAS
*Director of the United States Patent and Trademark Office*